United States Patent
Kim et al.

(10) Patent No.: US 7,825,405 B2
(45) Date of Patent: *Nov. 2, 2010

(54) DEVICES COMPRISING COATED SEMICONDUCTOR NANOCRYSTALS HETEROSTRUCTURES

(75) Inventors: Sungjee Kim, Pasadena, CA (US); Moungi G. Bawendi, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 69 days.

This patent is subject to a terminal disclaimer.

(21) Appl. No.: 12/213,001

(22) Filed: Jun. 12, 2008

(65) Prior Publication Data
US 2009/0301564 A1 Dec. 10, 2009

Related U.S. Application Data

(63) Continuation of application No. 10/638,546, filed on Aug. 12, 2003, now Pat. No. 7,390,568.

(60) Provisional application No. 60/402,726, filed on Aug. 13, 2002.

(51) Int. Cl.
*H01L 27/02* (2006.01)
*B32B 5/16* (2006.01)

(52) U.S. Cl. .................. 257/40; 257/42; 257/76; 257/E27.001; 257/E27.009; 257/E29.078; 428/403; 977/773

(58) Field of Classification Search .............. 428/403; 977/773; 257/40, 42, 76, E27.001, E27.009, 257/E29.078

See application file for complete search history.

(56) References Cited

U.S. PATENT DOCUMENTS

| | | | |
|---|---|---|---|
| 4,882,609 | A | 11/1989 | Schubert et al. |
| 5,021,360 | A | 6/1991 | Melman et al. |
| 5,081,511 | A | 1/1992 | Tehrani et al. |
| 5,262,357 | A | 11/1993 | Alivisatos et al. |
| 5,293,050 | A | 3/1994 | Chapple-Sokol et al. |
| 5,354,707 | A | 10/1994 | Chapple-Sokol et al. |
| 5,395,791 | A | 3/1995 | Cheng et al. |
| 5,412,231 | A | 5/1995 | Furuya |
| 5,422,489 | A | 6/1995 | Bhargava |
| 5,434,878 | A | 7/1995 | Lawandy |
| 5,481,397 | A | 1/1996 | Burt |

(Continued)

FOREIGN PATENT DOCUMENTS

WO WO 95/29473 11/1995

(Continued)

OTHER PUBLICATIONS

Aktsipetrov, O.A., et al. "Generation of reflected second harmonic at semiconductor quantum dots," *JETP Letters*, vol. 55, No. 8, 435-439 (1992).

(Continued)

*Primary Examiner*—H. (Holly) T Le
(74) *Attorney, Agent, or Firm*—Steptoe & Johnson LLP

(57) ABSTRACT

A semiconductor nanocrystal heterostructure has a core of a first semiconductor material surrounded by an overcoating of a second semiconductor material. Upon excitation, one carrier can be substantially confined to the core and the other carrier can be substantially confined to the overcoating.

19 Claims, 5 Drawing Sheets

U.S. PATENT DOCUMENTS

| | | | |
|---|---|---|---|
| 5,492,080 | A | 2/1996 | Ohkawa et al. |
| 5,499,260 | A | 3/1996 | Takahashi et al. |
| 5,505,928 | A | 4/1996 | Alivisatos et al. |
| 5,515,393 | A | 5/1996 | Okuyama et al. |
| 5,525,377 | A | 6/1996 | Gallagher et al. |
| 5,537,000 | A | 7/1996 | Alivisatos et al. |
| 5,541,948 | A | 7/1996 | Krupke et al. |
| 5,585,640 | A | 12/1996 | Huston et al. |
| 5,625,456 | A | 4/1997 | Lawandy |
| 5,677,545 | A | 10/1997 | Shi et al. |
| 5,747,180 | A | 5/1998 | Miller et al. |
| 5,751,018 | A | 5/1998 | Alivisatos et al. |
| 5,882,779 | A | 3/1999 | Lawandy |
| 5,985,173 | A | 11/1999 | Gray et al. |
| 5,985,353 | A | 11/1999 | Lawton et al. |
| 5,990,479 | A | 11/1999 | Weiss et al. |
| 6,114,038 | A | 9/2000 | Castro et al. |
| 6,139,585 | A | 10/2000 | Li |
| 6,207,229 | B1 * | 3/2001 | Bawendi et al. ............. 427/215 |
| 6,319,426 | B1 | 11/2001 | Bawendi et al. |
| 6,322,901 | B1 | 11/2001 | Bawendi et al. |
| 6,323,989 | B1 | 11/2001 | Jacobson et al. |
| 6,379,635 | B2 | 4/2002 | O'Brien et al. |
| 6,423,551 | B1 | 7/2002 | Weiss et al. |
| 6,444,143 | B2 | 9/2002 | Bawendi et al. |
| 6,447,698 | B1 | 9/2002 | Ihara et al. |
| 6,548,168 | B1 | 4/2003 | Mulvaney et al. |
| 6,548,171 | B1 | 4/2003 | Barbera-Guillem et al. |
| 6,592,842 | B2 | 7/2003 | Elder et al. |
| 6,685,909 | B2 * | 2/2004 | Elder et al. ................. 423/598 |
| 6,819,692 | B2 | 11/2004 | Klimov et al. |
| 6,861,155 | B2 | 3/2005 | Bawendi et al. |
| 7,060,243 | B2 | 6/2006 | Bawendi et al. |
| 7,253,452 | B2 * | 8/2007 | Steckel et al. ............... 257/103 |
| 7,390,568 | B2 * | 6/2008 | Kim et al. ................... 428/403 |
| 7,394,094 | B2 * | 7/2008 | Halpert et al. ................ 257/40 |
| 2002/0066401 | A1 | 6/2002 | Peng et al. |
| 2002/0071952 | A1 | 6/2002 | Bawendi et al. |
| 2003/0017264 | A1 | 1/2003 | Treadway et al. |

FOREIGN PATENT DOCUMENTS

| | | |
|---|---|---|
| WO | WO 98/04740 | 2/1998 |
| WO | WO 98/19963 | 5/1998 |
| WO | WO 98/33070 | 7/1998 |
| WO | WO 98/36376 | 8/1998 |
| WO | WO 98/46372 | 10/1998 |
| WO | WO 02/25745 | 3/2002 |

OTHER PUBLICATIONS

Alivisatos et al., "Organization of 'nanocrystal molecules' using DNA," Nature, 382:609-611, Aug. 15, 1996.

Alivisatos et al., "Semiconductor Clusters, Nanocrystals, and Quantum Dots," Science, 271:933-937, 1996.

Alivisatos, "Perspectives on the Physical Chemistry of Semiconductor Nanocrystals" J. Phys. Chem. 1996(100):13226-13239, 1996.

Baltrameyunas, R., et al.,"Fast switching of the transmission of light by glasses activated with CdS microcrystals," Sov. Phys. Semicond., vol. 25 No. 2, 164-166 (1991).

Baltramiejunas, R., et al. "Rapid Processes of Darkening and Bleaching in CdS Doped Glasses," Superlattices and Microstructures vol. 10, No. 3, 307-310 (1990).

Bawendi et al., "Luminescence properties of CdSe quantum crystallites: resonance between interior and surface localized states," J. Chem. Phys., 96(2):946-954, 1992.

Beverloo et al., "Preparation and Microscopic Visualization of Multicolor Luminescent Immunophosphors," Cytometry, 13:561-570, 1992.

Bhargava, R.N., et al., "Quantum Confined Atoms of Doped ZnO Nanocrystals", Phys. Stat. Sol (b) 229, No. 2, 897-901 (2002).

Bruchez et al., "Semiconductor Nanocrystals as Fluorescent Biological Labels" Science 281:2013-2016, Sep. 1998.

Bruchez et al., "Semiconductor nanocrystals as fluorescent probes for biology," Cytometry, Supplement 9, p. 26, Mar. 1998.

Bryant et al., "Designing quantum dots and quantum-dot solids," Physica E 2001, 11, 72-77.

Bunge, S.D. et al., J. Mater. Chem. 2003, 13 1705-1709.

Cao, Y.W. and Banin, U., Angew. Chem. Int. Edit. 1999, 38, 3692.

Chamarro, M., et al., "Enhancement of electron-hole exchange interaction in CdSe nanocrystals; A quantum confinement effect," Physical Review B, vol. 53, No. 3, Jan. 15, 1996-I, 1336-1342.

Chamarro, M., et al., "Enhancement of Exciton Exchange Interaction by Quantum Confinement in CdSe Nanocrystals," Jpn. J. Appl. Phys, vol. 34, 12-14 (1994).

Chamarro, M., et al., "Size-dependent Electron-Hole Exchange Interaction in CdSe Quantum Dots, Il Nuovo Cimento," vol. 17, Nos. 11-12, (1995) 1407-1412.

Chan et al., "Quantum Dot Bioconjugates for Ultrasensitive Nonisotopic Detection" Science 281:2016-2018, Sep. 1998.

Chepic, D.I., et al., "Auger ionization of semiconductor quantum drops in a glass matrix," Journal of Luminescence 47 (1990) 113-127 North-Holland.

Coffer et al., "Characterization of quantum-confined CdS Nanocrystallites stabilized by deoxyribonucleic acid (DNA)" Nanotechnology 3:69-76, 1992.

Colvin et al., "Light-emitting diodes made from cadmium selenide nanocrystals and a semiconducting polymer" Nature 370(6488):354-357, Aug. 4, 1994.

Correa-Duarte et al., "Stabilization of CdS semiconductor nanoparticles against photodegradation by silica coating procedure," Chem. Phys. Lett., 286:497-501, 1998.

Cumberland, S.L., et al., Chem. Mater. 2002, 14, 1576-1584.

Dabbousi et al., "Electroluminescence from CdSe quantum-dot/polymer composites" Appl. Phys. Lett. 66(11):1316-1318, Mar. 13, 1995.

Dabbousi, et al., "(CdSe)ZnS core-shell quantum dots: synthesis and characterization of a size series of highly luminescent nanocrystallites" J. of Phys. Chem. B 101(46):9463-9475, Nov. 13, 1997.

Danek et al., "Synthesis of Luminescent Thin-Film CdSe/ZnSe Quantum Dot Composites Using CdSe Quantum Dots Passivated with an Overlayer of ZnSe" Chem. Mater. 8(1):173-180, 1996.

de Oliveira et al."Probing of the quantum dot size distribution in CdTe-doped glasses by photoluminescence excitation spectroscopy," Appl. Phys. Lett. 66:439-441 (1995).

De Paula et al. "Quantum confinement effects on the optical phonons of CdTe quantum dots," Superlattices and Microstructures 23:1103-1106 (1998).

Dneproviskii, V.S., et al., "Time-Resolved Luminescence of CdSe Microcrystals," Solid State Communications, vol. 74, No. 7, pp. 555-557, 1990.

Edamatsu, K., et al., "Subpicosecond dynamics of confined excitons and optical nonlinearities of CuC1 quantum dots," Journal of Luminescence 66 & 67 (1996) 406-409.

Efros, A.L., et al., "Resonance Raman Spectroscopy of Electron-Hole Pairs—Polar Phonon Coupling in Semiconductor Quantum Microcrystals," Solid State Communications, vol. 78, No. 10, pp. 853-856, 1991.

Ekimov, A. I., et al., "Absorportion and intensity-dependent photoluminescence measurements on CdSe quantum dots: assignment of the first electronic transitions," Journal of the Optical Society of America, vol. 10, Nos. 1-12, 100-107 (1992).

Ekimov, A., et al., "Growth of CdSe nanocrystals in ion-implanted $SiO_2$ films," Journal of Crystal Growth 151 (1995) 38-45.

Ekimov, A.I., "Growth and optical properties of semiconductor nanocrystals in a glass matrix," Journal of Luminescence 70 (1996) 1-20.

Ekimov, A.I., "Optical Properties of Oxide Glasses Doped by Semiconductor Nanocrystals," Radiation Effects and Defects in Solids, 1995, vol. 134, pp. 11-22.

Ekimov, A.I., "Optical Properties of Semiconductor Quantum Dots in Glass Matrix," Physica Scripta. vol. T39, 217-222 (1991).

Ekimov, A.I., et al. "Dimensional Effects in Luminescence Spectra of Zero-Dimensional Semiconductor Structures," *Bulletin of the Russian Academy of Sciences*, vol. 56, No. 2, pp. 154-157, Feb. 1992.

Ekimov, A.I., et al., "Spectra and Decay Kinetics of Radiative Recombination in CdS Microcrystals," *Journal of Luminescence* 46 (1990) 83-95 North-Holland.

Ekimov, A.I., et al., "Donor-like Exciton in Zero-Dimension Semiconductor Structures," *Solid State Communications*, vol. 69, No. 5, pp. 565-568, 1989.

Ekimov, A.I., et al., "Influence of high hydrostatic pressures on the exciton spectrum of CdS microcrystals in glass," *Sov. Phys. Semicond.* 23(9), Sep. 1989, pp. 965-966.

Ekimov, A.I., et al., "Nonlinear Optics of Semiconductor-Doped Glasses," *Phys. Stat. Sol.* (b) 150, (1988) pp. 627-633.

Ekimov, A.I., et al., "Optics of Zero Dimensional Semiconductor Systems, *Acta Physica Polonica A*," vol. 79 (1991), No. 1. pp. 5-14.

Ekimov, A.I., et al., "Photoluminescence of quasizero-dimensional semiconductor structures," *Sov. Phys. Solid State* 31(8), Aug. 1989, pp. 1385-1393.

Ekimov, A.I., et al., "Quantization of the energy spectrum of holes in the adiabatic potential of the electron," *JETP Lett.*, vol. 43, No. 6, Mar. 25, 1986, pp. 376-379.

Ekimov, A.I., et al., "Quantum Size Effect in Semiconductor Microcrystals," *Solid State Communications*, vol. 56, No. 11, pp. 921-924, 1985.

Ekimov, A.I., et al., "Quantum size effect in the optical spectra of semiconductor microcrystals," *Sov. Phys. Semicond.* 16(7), Jul. 1982, pp. 775-778.

Ekimov, A.I., et al., "Quantum size effect in three-dimensional microscopic semiconductor crystals," *JETP Lett*, vol. 34, No. 6, Sep. 20, 1981, pp. 345-349.

Ekimov, A.I., et al., "Quantum-Size Stark Effect in Semiconductor Microcrystals," *Journal of Luminescence* 46 (1990) 97-100 North-Holland.

Ekimov, A.I., et al., "Size quantization of the electron energy spectrum in a microscopic semiconductor crystal," *JETP Lett.*, vol. 40, No. 8, Oct. 25, 1984, pp. 1136-1139.

Empedocles et al, "Photoluminescence Spectroscopy of Single CdSe Nanocrystallite Quantum Dots" *Phys. Rev. Lett.* 77(18):3873-3876, Oct. 1996.

Empedocles et al., "Quantum-Confined Stark Effect in Single CdSe Nanocrystallite Quantum Dots" *Science* 278:2114-2117, Dec. 1997.

Gan et al., "Enhanced Photoluminescence and Characterization of Mn-Doped ZnS Nanocrystallites Synthesized in Microemulsion" *Langmuir* 1997(13):6427-6431, 1997.

Gao et al., "Strongly Photoluminescent CdTe Nanocrystals by Proper Surface Modification," J. Phys. Chem., 102:8360-8363, 1998.

Gopidas, K.R., Bohorquez, M. Kamat, P.V. "Photophysical and Photochemical Aspects of Coupled Semiconductors. Charge-Transfer Processes in Colloidal CdS-TiO$_2$ and CdS-AgI Systems," *J. Phys Chem.* 1990, 94, 6435-6440.

Grabovskis, V.Y., et al., "Photoionization of semiconducting microcrystals in glass," *Sov. Phys. Solid State* 31(1), Jan. 1989, pp. 149-151.

Guha et al., "Hybrid organic-inorganic semiconductor-based light-emitting diodes" *J. Appl. Phys.* 82(8):4126-4128, Oct. 15, 1997.

Gurevich, S.A., et al. "Preparation and investigation of SIO$_2$ films activated by CdS semiconductor nanocrystals," *Soviet Physics Semiconductors*, vol. 26, 57-59 (1992).

Gurevich, S.A., et al., "Growth of CdS nanocrystals in silicate glasses and in thin SIO$_2$ films in the Initial states of the phase separation of a solid solution," *Semiconductors*, 28 (5), May 1994, 486-493.

Hässelbarth, A, et al. "Chemistry and Photophysics of Mixed CdS/HgS Colloids," *J. Phys. Chem.* 1993, 97, 53330-5340.

Hässelbarth, A, Eychmüller, A., and Weller, H. "Detection of shallow electron traps in quantum sized CdS by fluorescence quenching experiments," *Chem. Phys. Lett.* 1993, 203, 271-276.

Hatami et al., "Carrier dynamics in type-II GaSb/GaAs quantum dots", Physical Review B, vol. 57, No. 8, Feb. 1998, 4635-4641.

Haus, J.W., et al., *Phys. Rev. B* 1993, 47, 1359.

Hines et al., "Synthesis and Characterization of Strongly Luminescing ZnS-Capped CdSe Nanocrystals" *J. Phys. Chem.* 100:468-471, Jan. 1996.

Itoh, T. et al., "Interface effects on the properties of confined excitons in CuCl microcrystals," *Journal of Luminescence* 60 & 61 (1994) 396-399.

Itoh, T., et al., "Polaron and Exciton-Phonon Complexes in CuCl Nanocrystals," *Physical Review Letters*, vol. 74, No. 9, Feb. 27, 1995, p. 1645-1648.

Itoh, T., et al., "Subpicosecond dynamics of confined excitons in CuCl nanocrystals," *Materials Science and Engineering* A217/218 (1996) 167-170.

Jarvis et al., "Solution Synthesis and Photoluminescence Studies of Small Crystallites of Cadmium Telluride," Mat. Res. Soc. Symp. Proc., 272:229-234, 1992.

Jursenas, S., et al., "Surface Recombination of Nonequilibrium Electron-Hole Plasma in Laser-Modified Semiconductor-Doped Glasses," *Solid State Communications*, vol. 87, No. 6, 577-580 (1993).

Kagan et al., "Electronic Energy Transfer in CdSe Quantum Dot Solids," Physical Review Letters, 76:1517-1520, 1996.

Kagan et al., "Long-range resonance transfer of electronic excitations in close-packed CdSe quantum-dot solids," Physical Review Letters, 54:8633-8643, Sep. 15, 1996.

Kamat, P.V. "Photoinduced Charge Transfer between Fullerenes ($C_{60}$ and $C_{70}$) and Semiconductor ZnO Colloids," *J. Am. Chem. Soc.* 1991, 113, 9705-9707.

Kietzmann, R. et al. "Picosecond Time Resolved Electron Injection from Excited Cresyl Violet Monomers and $Cd_3P_2$ Quantum Dots into $TiO_2$," *Mol. Cryst. Liq. Cryst.* 1991, 194, 169-180.

Kim et al., "Type-II Quantum Dots: CdTe/CdSe(Core/Shell) and CdSe/ZnTe(Core/Shell) Heterostructures", J. Am. Chem. Soc. 2003, 125, 11466-11467.

Kortan et al., "Nucleation and Growth of CdSe on ZnS Quantum Crystallite Seeds, and Vice Versa, in Inverse Micelle Media" *J. Am Chem. Soc.* 112:1327-1332, 1990.

Kuno et al., "The band edge luminescence of surface modified CdSe nanocrystallites: Probing the luminescing state" *J. Chem. Phys.* 106(23):9869-9882, Jun. 1997.

Kuroda et al. "Micro photoluminescence spectra of CdTe and CdMnTe self-organized quantum dots," *Journal of Luminescence* 83-84:321-342 (1999).

Laheld, U.E.H., et al., *Phys. Rev. B* 1995, 52:2697.

Lawless et al., "Bifunctional Capping of CdS Nanoparticles and Bridging to TiO2" *J. Phys. Chem.* 99:10329-10335, 1995.

Lee et al., "Surface Derivatization of Nanocrystalline CdSe Semiconductors," Mat. Res. Soc. Symp. Proc., 452:323-328, 1997.

Liz-Marzan et al., "Synthesis of Nanosized Gold-Silica Core-Shell Particles" *Langmuir* 12:4329-4335, 1996.

Löher et al., "Epitaxy films of the 3D semiconductor CdS on the 2D layered substrate MX2 prepared by Van der Waals epitaxy" Journal of Crystal Growth, vol. 146, 1995, pp. 408-412.

Lublinskaya, O., et al., "CdS nanocrystal growth in thin silica films: evolution of size distribution function", *Journal of Crystal Growth* 184/185 (1998) 360-364.

Mahtab et al., "Preferential-absorption of a 'kinked' DNA to a neutral curved surface: comparison to and implications for nonspecific DNA-protein interactions," *J. Am. Chem. Soc.*, 118:7028-7032, 1996.

Mahtab et al., "Protein-sized quantum dot luminescence can distinguish between 'straight', 'bent', and 'kinked' oligonucleotides", *Am. Chem. Soc.*, 117:9099-9100, 1995.

Matsumoto et al., "Preparation of Monodisperse CdS Nanocrystals by Size Selective Photocorrosion" *J. Phys. Chem.*100(32):13781-13785, 1996.

Mikulec et al., "Fluorescent semiconductor nanocrystallites derivatized with biomolecules" *Amer. Chem.. Soc. Nat'l Meeting*, Boston, MA, Aug. 24, 1998.

Mikulec et al., "Synthesis and Characterization of Highly Luminescent (CdSe)ZnS Quantum Dots," Materials Research Society Symposium, 452:359-364, 1997.

Mokari, T. and Banin, U. "Synthesis and Properties of CdSe/ZnS Core/Shell Nanorods", Institute of Chemistry, The Hebrew University of Jerusalem, (2003).

Müllenborn et al., "Characterization of Solution-Synthesized CdTe and HgTe," Applied Physics, 56:317-321, 1993.

Mulvaney, P., Giersig, M., Henglein, A. "Surface Chemistry of Colloidal Gold: Deposition of Lead and Accompanying Optical Effects," *J. Phys. Chem.* 1992, 96, 10419-10424.

Murphy et al., "Quantum dots as inorganic DNA-binding proteins," *Mat. Res. Soc. Symp.*, 452:597-600, 1997.

Murray et al., "Synthesis and Characterization of Nearly Monodisperse CdE (E=S, Se, Te) Semiconductor Nanocrystallites" *J. Am. Chem. Soc.* 115(19):8706-8715, 1993.

Nirmal et al., "Fluorescence Intermittency in single Cadmium Selenide Nanocrystals" *Nature* 383:802-804, Oct. 1996.

Pehnt et al., "Nanoparticle Precursor Route to Low-Temperature Spray Deposition of CdTe Thin Films," *Appl. Phys. Lett.*, 67(15):2176-2178, 1995.

Peng et al., "Epitaxial Growth of Highly Luminescent CdSe/CdS Core/Shell Nanocrystals with Photostability and Electronic Accessibility," J. Am. Chem. Soc., 119:7019-7029, 1997.

Peng et al., "Synthesis and Isolation of a Homodimer of Cadmium Selenide Nanocrystals," Angewandte Chemie, 36:145-147, 1997.

Rajh et al., "Synthesis and Characterization of Surface-Modified Colloidal CdTe Quantum Dots" *J. Phys. Chem.* 97:11999-12003, Nov. 1993.

Resch et al., "Photochemistry and Radiation Chemistry of Colloidal Semiconductors. 33. Chemical Changes and Fluorescence in CdTe and ZnTe," *Langmuir* 5:1015-1020 (1989).

Rockenberger et al. "An EXAFS Study on Thiolcapped CdTe Nanocrystals," *Ber. Bunsenges. Phys. Chem.* 102:1561-1564 (1998).

Rogach et al. "Synthesis, Morphology and Optical Properties of Thiol-Stabilized CdTe Nanoclusters in Aqueous Solution," *Ber. Bunsenges. Phys. Chem.* 101:1668-1670 (1997).

Rogach et al., "Synthesis and characterization of Thiol-Stabilized CdTe Nanocrystals" *Ber. Bunsenges. Phys. Chem.* 100(11):1772-2778, 1996.

Rorison, J.M., *Phys. Rev. B* 1993, 48:4643.

Rorison, "A theory for excitons in type II quantum dot systems", Semicond. Sci. Technol. 8 (1993) 1470-1474.

Saviot, L., et al., "Effects of Resonance on Low-Frequency Raman Scattering From Semiconductor Nanocrystals," *Radiation Effects and Defects in Solids*, 1995, vol. 137, pp. 45-50.

Saviot, L., et al., "Size dependence of acoustic and optical vibrational modes of CdSe nanocrystals in glasses," *Journal of Non-Crystalline Solids* 197 (1996) 238-246.

Saviot, L., et al., "Size-selective resonant Raman scattering in CdS doped glasses," *Physical Review B*, vol. 57, No. 1, Jan. 1, 1998-I, 341-346.

Schittenhelm, P., et al., *Appl. Phys. Lett.* 1995, 67, 1292.

Schooss, D., et al., *Phys. Rev. B* 1994, 49, 49.

Sirenko, A.A., et al., "Spin-flip and acoustic-phonon Raman scattering in CdS nanocrystals", *Physical Review B*, vol. 58, No. 4, 15 (Jul. 1998-II), 2077-2087.

Spanhel et al., "Photochemistry of Colloidal Semiconductors. Surface Modification and Stability of Strong Luminescing CdS Particles" *J. Am. Chem. Soc.* 109(19):5649-5655, 1987.

Spanhel, L., Henglein, A., Weller, H. "Photochemistry of Semiconductor Colloids. 24. Interparticle Electron Transfer in $Cd_3P_2$-$TiO_2$ and $Cd_3P_2$-ZnO Sandwich Structures," *Ber. Bunsenges. Phys. Chem.* 1987, 91, 1359-1363.

Spanhel, L., Weller, H., Henglein, A. "Photochemistry of Semiconductor Colloids. 22. Electron Injection from Illuminated CdS into Attached $TiO_2$ and ZnO Particles," *J. Am. Chem. Soc.* 1987, 109, 6632-6635.

Steigerwald et al., "Surface Derivatization and Isolation of Semiconductor Cluster Molecules," J. Am. Chem. Soc., 110:3046-3050, 1988.

Suzuki, K., et al., *J. Appl. Phys.* 1999, 85, 8349.

Tamulaitis, G., et al., "Dynamics of Nonlinear Optical Response of CuBr-Doped Glasses," *Superlattices and Microstructures*, vol. 3, No. 2, 199-202 (1993).

Tsuji et al., "Characterization of CdS thin film in high efficient CdS/CdTe solar cells", Journal of Crystal Growth, vol. 214/215, 2000, pp. 1142-1147.

Valenta, J., et al., "Dynamics of excitons in CuBr nanocrystals: Spectral-hole burning and transient four-wave-mixing measurements," *Physical Review B*, vol. 57, No. 3, Jan. 15, 1998-I, 1774-1783.

Vandyshev, Y.V., et al., "Nonlinear optical properties of semiconductor microcrystals," *JETP Lett.*, vol. 46, No. 10, Nov. 25, 1987 pp. 435-439.

Volkov, A.S., et al., "Oscillations of polarization of recombination radiation of a variable gap semiconductor in a magnetic field," *JETP Lett.*, vol. 25 No. 55, 526-528 (1977).

Weller, H. "Quantized Semiconductor Particles: A Novel State of Matter for Materials Science," *Adv. Mater.* 1993, 5, 88-95.

Whitesell et al., "Directionally Aligned Helical Peptides on Surfaces" *Science* 261:73-76, Jul. 1993.

Yakimov, A.I., et al., *Phys. Rev. B* 2001, 63, 045312.

Yang, C.S., et al., *Chem. Mater.* 2002, 14, 1277-1284.

Mikulec, F.V., "Synthesis and Characterizations of Highly Luminescent (CDSE) ZNS Quantum Dots", Jan. 1, 1997, Materials Research Society Symopsium Proceedings, vol. 452, pp. 359-364.

* cited by examiner

DEVICES COMPRISING COATED SEMICONDUCTOR NANOCRYSTALS HETEROSTRUCTURES

CLAIM OF PRIORITY

This application is a continuation of U.S. application Ser. No. 10/638,546, filed Aug. 12, 2003 which claims priority to U.S. Patent Application Ser. No. 60/402,726, filed on Aug. 13, 2002, the entire contents of which are hereby incorporated by reference.

FEDERALLY SPONSORED RESEARCH OR DEVELOPMENT

The U.S. Government may have certain rights in this invention pursuant to Contract No. N00014-01-1-0787 awarded by the Office of Naval Research.

TECHNICAL FIELD

The invention relates to semiconductor nanocrystal heterostructures.

BACKGROUND

Semiconductor nanocrystals have been a subject of great interest, promising extensive applications including display devices, information storage, biological tagging materials, photovoltaics, sensors and catalysts. Nanocrystals having small diameters can have properties intermediate between molecular and bulk forms of matter. For example, nanocrystals based on semiconductor materials having small diameters can exhibit quantum confinement of both the electron and hole in all three dimensions, which leads to an increase in the effective band gap of the material with decreasing crystallite size. Consequently, both the optical absorption and emission of nanocrystals shift to the blue (i.e., to higher energies) as the size of the crystallites decreases.

The quantum efficiency of emission from nanocrystals having a core of a first semiconductor material can be enhanced by applying an overcoating of a second semiconductor material such that the conduction band of the second semiconductor material is of higher energy than that of the first semiconductor material, and the valence band of the second semiconductor material is of lower energy than that of the first semiconductor material. As a result, both carriers, i.e., electrons and holes, are confined in the core of the nanocrystal.

SUMMARY

In general, a semiconductor nanocrystal heterostructure has a core of a first semiconductor material surrounded by an overcoating of a second semiconductor material. The first semiconductor material and second semiconductor material are selected so that, upon excitation, one carrier is substantially confined to the core and the other carrier is substantially confined to the overcoating. In one example, the conduction band of the first semiconductor material is at higher energy than the conduction band of the second semiconductor material and the valence band of the first semiconductor material is at higher energy than the valence band of the second semiconductor material. In another example, the conduction band of the first semiconductor material is at lower energy than the conduction band of the second semiconductor material and the valence band of the first semiconductor material is at lower energy than the valence band of the second semiconductor material. These band alignments make spatial separation of carriers, i.e. the hole and the electron, energetically favorable upon excitation. These structures are type II heterostructures. In contrast, the configurations in which the conduction band of the second semiconductor material is of higher energy than that of the first semiconductor material, and the valence band of the second semiconductor material is of lower energy than that of the first semiconductor material are type I heterostructures. Type I heterostructure nanocrystals favor confinement of both the hole and the electron in the core. The language of type I and type II is borrowed from the quantum well literature where such structures have been extensively studied.

Nanocrystals having type II heterostructures have advantageous properties that result of the spatial separation of carriers. In some nanocrystals having type II heterostructures the effective band gap, as measured by the difference in the energy of emission and energy of the lowest absorption features, can be smaller than the band gap of either of the two semiconductors making up the structure. By selecting particular first semiconductor materials and second semiconductor materials, and core diameters and overcoating thicknesses, nanocrystals having type II heterostructures can have emission wavelengths, such as infrared wavelengths, previously unavailable with the semiconductor of the nanocrystal core in previous structures. In addition, the separation of charges in the lowest excited states of nanocrystals having type II heterostructures can make these materials more efficient in photovoltaic or photoconduction devices where the nanocrystals are chromophores and one of the carriers needs to be transported away from the excitation site prior to recombination.

Advantageously, a wide variety of nanocrystals having type II heterostructures can be prepared using colloidal synthesis. Colloidal synthesis allows nanocrystals to be prepared with controllable dispersibility imparted from coordinating agents, such as ligands, and are prepared in the absence of wetting layers commonly employed in nanocrystals having type II heterostructures prepared by molecular beam epitaxy.

In one aspect, a method of preparing a coated nanocrystal includes introducing a core nanocrystal including a first semiconductor material into an overcoating reaction mixture and overcoating a second semiconductor material on the core nanocrystal, wherein the first semiconductor material and the second semiconductor material are selected so that, upon excitation, one carrier is substantially confined to the core and the other carrier is substantially confined to the overcoating. In another aspect, a coated nanocrystal includes a core nanocrystal including a first semiconductor material, an overcoating including a second semiconductor material on the core nanocrystal, and an organic layer on a surface of the coated nanocrystal, wherein the first semiconductor material and the second semiconductor material are selected so that, upon excitation, one carrier is substantially confined to the core and the other carrier is substantially confined to the overcoating. In another aspect, a population of coated nanocrystals includes a plurality of coated nanocrystals, each coated nanocrystal including a core nanocrystal and an overcoating on each core nanocrystal, wherein each core includes a first semiconductor material and each overcoating includes a second semiconductor material, the plurality of core nanocrystals forming a population of nanocrystals, wherein the first semiconductor material and the second semiconductor material are selected so that, upon excitation, one carrier is substantially confined to the core and the other carrier is substantially confined to the overcoating, and the plurality of nanocrystals is monodisperse. In another aspect, a coated nanocrystal includes a core nanocrystal including a first semiconductor material, a first overcoating including a second semiconductor material on the core nanocrystal, and a second overcoating including a third semiconductor material on the first overcoating.

The conduction band of the first semiconductor material can be at higher energy than the conduction band of the second semiconductor material, and the valence band of the first semiconductor material can be at higher energy than the valence band of the second semiconductor material. The conduction band of the first semiconductor material can be at lower energy than the conduction band of the second semiconductor material, and the valence band of the first semiconductor material can be at lower energy than the valence band of the second semiconductor material. The nanocrystal can include an organic layer on a surface of the coated nanocrystal.

The method can include exposing the nanocrystal to an organic compound having affinity for a surface of the coated nanocrystal. The coated nanocrystal can be dispersible in a liquid. The first semiconductor material can be a Group II-VI compound, a Group II-V compound, a Group III-VI compound, a Group III-V compound, a Group IV-VI compound, a Group I-III-VI compound, a Group II-IV-VI compound, or a Group II-IV-V compound. The first semiconductor material can be ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, or mixtures thereof. The second semiconductor material can be a Group II-VI compound, a Group II-V compound, a Group III-VI compound, a Group III-V compound, a Group IV-VI compound, a Group I-III-VI compound, a Group II-IV-VI compound, or a Group II-IV-V compound. The second semiconductor material can be ZnO, ZnS, ZnSe, ZnTe, CdO, CdS, CdSe, CdTe, MgO, MgS, MgSe, MgTe, HgO, HgS, HgSe, HgTe, AlN, AlP, AlAs, AlSb, GaN, GaP, GaAs, GaSb, InN, InP, InAs, InSb, TlN, TlP, TlAs, TlSb, TlSb, PbS, PbSe, PbTe, or mixtures thereof. The first semiconductor material can be CdTe and the second semiconductor material CdSe. The first semiconductor material can be CdSe and the second semiconductor material ZnTe. The method can include overcoating a third semiconductor material on the second semiconductor material.

The third semiconductor material can have a mismatched band offset compared to the second semiconductor material. The third semiconductor material can be a Group II-VI compound, a Group II-V compound, a Group III-VI compound, a Group III-V compound, a Group IV-VI compound, a Group I-III-VI compound, a Group II-IV-VI compound, or a Group II-IV-V compound. The third semiconductor material can be ZnO, ZnS, ZnSe, ZnTe, CdO, CdS, CdSe, CdTe, MgO, MgS, MgSe, MgTe, HgO, HgS, HgSe, HgTe, AlN, AlP, AlAs, AlSb, GaN, GaP, GaAs, GaSb, InN, InP, InAs, InSb, TlN, TlP, TlAs, TlSb, TlSb, PbS, PbSe, PbTe, or mixtures thereof.

The nanocrystal can emit light upon excitation, wherein the wavelength of maximum emission intensity is longer than 700 nm, or between 700 nm and 1500 nm. The nanocrystal can have a quantum efficiency greater than 10%.

Other features, objects, and advantages of the invention will be apparent from the description and drawings, and from the claims.

DETAILED DESCRIPTION

Colloidal synthesis of nanocrystals can be used to manufacture nanocrystals that have core and overcoating (core-shell) structures and have type II heterostructures. Colloidal synthesis is described, for example, in Murray, C. B., et al., *J. Am. Chem. Soc.* 1993, 115, 8706, Peng, X., et al., *J. Am. Chem. Soc.* 1997, 119, 7019, Dabbousi, B. O., et al., *J. Phys. Chem. B* 1997, 101, 9463, and Cao, Y. W. and Banin, U., *Angew. Chem. Int. Edit.* 1999, 38, 3692, each of which is incorporated by reference in its entirety. The colloidal synthetic route can be applied to any II-VI and III-V semiconductor materials.

Figure 1:
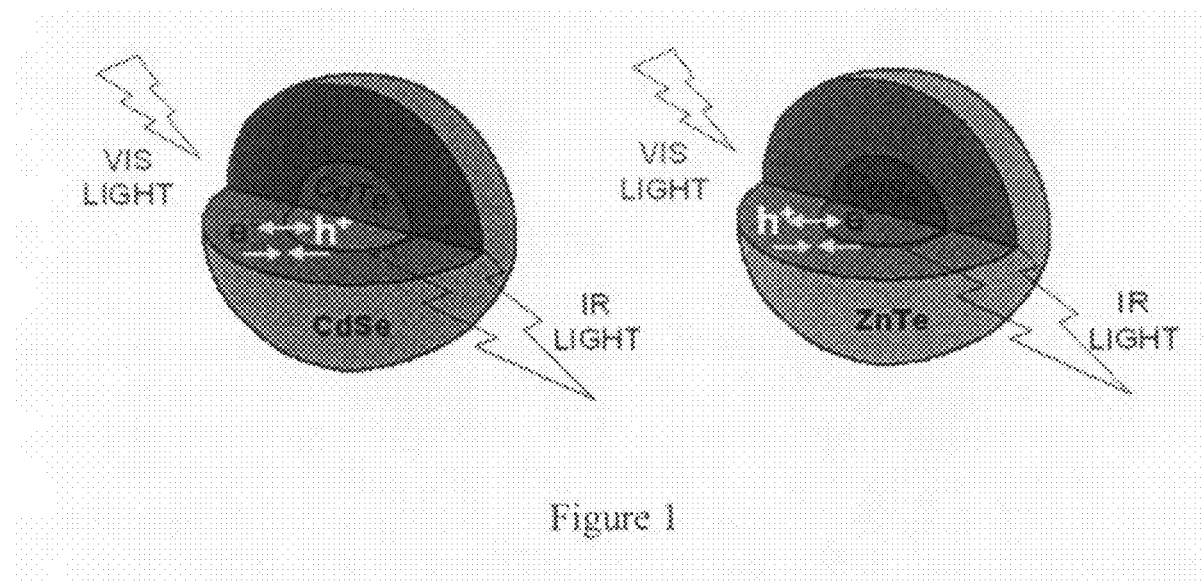
FIG. 1 is a drawing depicting a semiconductor nanocrystal having a type II heterostructure.

Examples of semiconductor nanocrystals having type II structures are shown in FIG. 1. Upon excitation of a nanocrystal having a type II heterostructure, the carriers are not confined in one semiconductor material. A nanocrystal having a type II heterostructure includes a core nanocrystal of one semiconductor surrounded by a shell of a second semiconductor. One carrier can become confined to the core, while the other is mostly confined to the shell. As illustrated in FIG. 1, the relative location of the carriers can depend on the materials in the core and the shell. The band offsets of the two semiconductor materials can make spatial separation of the hole and the electron energetically favorable. Nanocrystals having type II heterostructures can have novel properties because of the spatial separation of carriers, which does not occur in nanocrystals having type I heterostructures. Nanocrystals having type II structures can access emission wavelengths (i.e. wavelengths of maximum emission intensity) that would not otherwise be available with the semiconductors making up the nanocrystal.

GaSb/GaAs and Ge/Si type II nanocrystals grown by molecular beam epitaxy (MBE) have been studied. See, for example, Suzuki, K., et al., *J. Appl. Phys.* 1999, 85, 8349, and Schittenhelm, P., et al., *Appl. Phys. Lett.* 1995, 67, 1292, each of which is incorporated by reference in its entirety. However, studies of such type II nanocrystals are rather scarce presumably due to the synthetic difficulties. Colloidal synthesis can allow easy and flexible size-tuning of nanocrystals and advantageously provides a simple route to type II structures: CdTe/CdSe (core/shell) and CdSe/ZnTe (core/shell) type II nanocrystals. One advantage of colloidal synthesis is that there is no interference from wetting layers which is commonly observed in MBE-grown type II nanocrystals.

Figure 2:
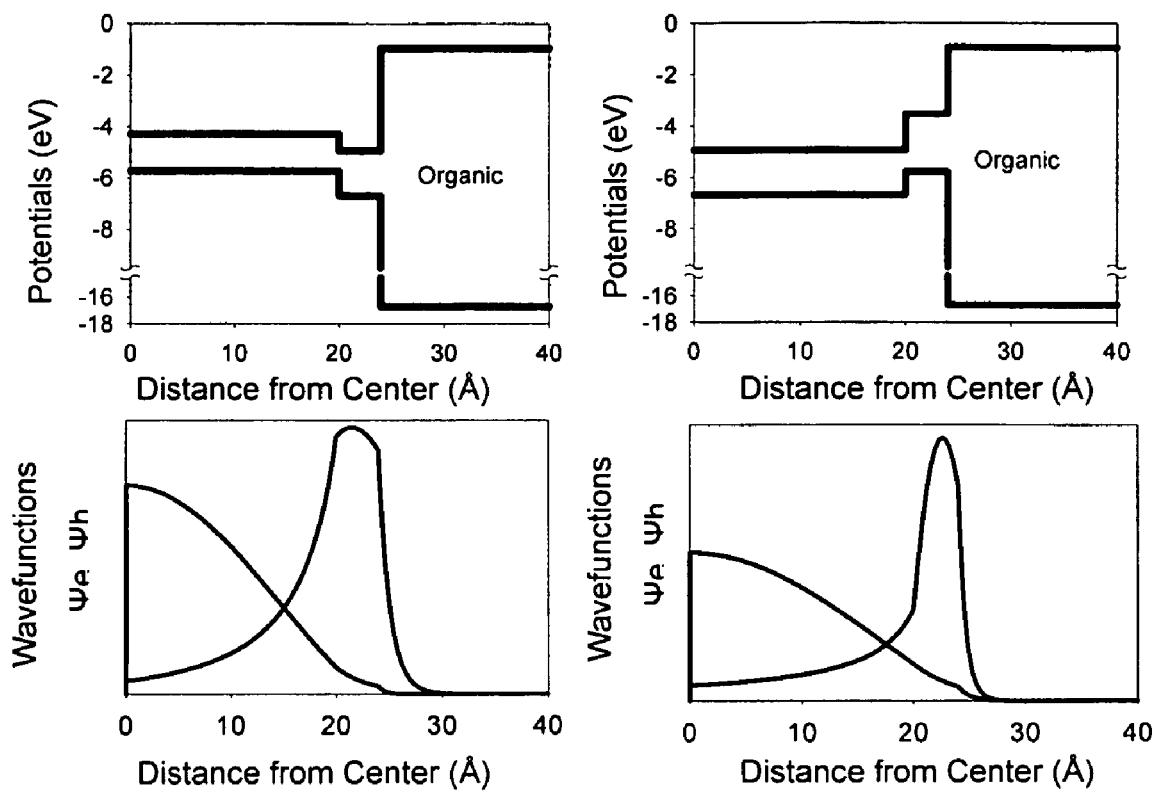
FIG. 2 is a drawing depicting potential diagrams and theoretically modeled electron (dotted line) and hole (solid line) radial wavefunctions for semiconductor nanocrystal heterostructures.

FIG. 2 shows the potential energy diagrams of CdTe/CdSe (core/shell) (left side) and CdSe/ZnTe (core/shell) (right side) nanocrystals with theoretically modeled radial wavefunctions for the lowest energy electron (dotted line) and hole (solid line) wave functions. The potentials are referenced to vacuum level and are not to scale. For the theoretical modeling, bulk material parameters were used with the electron and the hole wavefuctions which satisfy both the wavefunctions and the probability current continuities. See, for example, Haus, J. W., et al., *Phys. Rev. B* 1993, 47, 1359, Schooss, D., et al., *Phys. Rev. B* 1994, 49, 49, and Yakimov, A. I., et al., *Phys. Rev. B* 2001, 63, 045312, each of which is incorporated by reference in its entirety. A 20 Å core radius and 4 Å shell thickness was used for the modeling of both CdTe/CdSe (core/shell) and CdSe/ZnTe (core/shell) nanocrystals. In CdTe/CdSe (core/shell) nanocrystals, the counduction band of the shell is intermediate in energy to the valence band and conduction band of the core. CdTe/CdSe (core/shell) nanocrystals have lower potentials for the holes in the core and for the electrons in the shell. As a result, the holes can be mostly confined to the CdTe core, while the electrons can be mostly confined to the CdSe shell. The modeled wavefunctions of a CdTe/CdSe (core/shell) nanocrystal (FIG. 2), show that the hole wavefunction resides mostly in the core, while the electron wavefunction resides mostly in the shell. In contrast, CdSe/ZnTe (core/shell) nanocrystals have the opposite band offset alignment, with the valence band of the shell intermediate in energy to the valence band and conduction band of the core. As a result, the electrons reside mostly in the CdSe cores, while the holes reside mostly in the ZnTe shells. See FIG. 2.

CdTe and CdSe cores can be prepared by the pyrolysis of organometallic precursors in hot coordinating agents. See, for example, Murray, C. B., et al., *J. Am. Chem. Soc.* 1993, 115, 8706, and Mikulec, F., Ph.D. Thesis, MIT, Cambridge, 1999, each of which is incorporated by reference in its entirety. Growth of CdSe and ZnTe shell layers on the bare CdTe and CdSe cores can be carried out by simple modifications of conventional overcoating procedures. See, for example, Peng, X., et al., *J. Am. Chem. Soc.* 1997, 119, 7019, Dabbousi, B. O., et al., *J. Phys. Chem. B* 1997, 101, 9463, and Cao, Y. W. and Banin U. *Angew. Chem. Int. Edit.* 1999, 38, 3692, each of which is incorporated by reference in its entirety. For example, dimethylcadmium and bis(trimethylsilyl)selenide can be used for CdSe shell growth. A typical protocol for CdSe shell growth for CdTe/CdSe(core/shell) nanocrystals can include dispersing precipitated CdTe nanocrystals in trioctylphosphine oxide (TOPO), which has been dried under vacuum at 160° C., preparing an overcoating stock solution by mixing of dimethylcadmium and bis(trimethylsilyl)selenide in a 1:1 stoichiometry in trioctylphosphine (TOP), and adding the overcoating stock solution to the CdTe nanocrystal-TOPO mixture at a temperature of between 80° C. and 180° C., depending on the size of CdTe nanocrystals used. The mixture can be maintained at this temperature until small nanocrystals (as monitored by optical spectroscopy) of the overcoating form in the mixture, for example three hours. The mixture can be brought to a higher temperature, e.g. 200° C., and held there for a period of hours to days, until the overcoating is formed. A higher temperature can be necessary for larger size nanocrystals. ZnTe shell growth can be obtained by a similar method using diethylzinc and trioctylphosphine telluride precursors. The cores having a desired average diameter can be obtained from the initial core preparations, and the thickness of the shell layers can be controlled by the amount of the precursors used at the subsequent growth step.

Spatial separation of the carriers in type II nanocrystals suggests poor overlap between the electron and hole wavefunctions, preventing type II nanocrystals from reaching high emission quantum efficiencies. In the case of CdTe/CdSe (core/shell) nanocrystals, quantum efficiency of up to 4% was obtained. CdSe/ZnTe (core/shell) nanocrystals have quantum efficiency of less than 1%. The lower quantum efficiency of CdSe/ZnTe (core/shell) can be due to smaller overlap between the electron and hole wavefunctions than the overlap in of CdTe/CdSe (core/shell) nanocrystals. Holes confined in the shells, as in the case of CdSe/ZnTe (core/shell) nanocrystals, have a larger effective mass than electrons and therefore tend to spread less into the cores. See FIG. 2. Moreover, a system with the holes confined in the shells like CdSe/ZnTe (core/shell) nanocrystals may be more susceptible to trap sites.

The photoluminescence emissions from type II heterostructure nanocrystals, such as CdTe/CdSe (core/shell) and CdSe/ZnTe (core/shell) nanocrystals, can occur at longer wavelengths than emmission from the corresponding cores. The emission from nanocrystals having type II structures originates from the radiative recombination of the carriers across the core-shell interface. Therefore, the energy of the emission depends on the band offsets, which are controlled by the core semiconductor material and size and the overcoating semiconductor material and thickness. Type II nanocrystals can have a smaller effective bandgap, and therefore emit at longer wavelengths, than nanocrystals composed of either the core or shell material in the type II nanocrystal. The nanocrystals having type II structures can be considered to have quasi-indirect, or virtual, bandgaps whose energies are determined by the band offsets. The effective bandgap can be engineered in such structures, since many possible combinations of semiconductor materials can be used to tailor the virtual bandgaps.

To overcome the limitation of quantum efficiency in nanocrystals having type II structures, additional layers of semiconductor materials can be added to the particles. For example, a second coating of ZnTe can be added to a CdTe/CdSe (core/shell) nanocrystal, and increase the quantum efficiency to as high as 20%. The overcoating procedure can be similar to the CdSe/ZnTe (core/shell) nanocrystal shell preparation. The enhanced quantum efficiency is thought to originate from the increased carrier wavefunction overlap induced by the mismatched bandgaps. For increased quantum efficiency, it can be important for the first coating and second coating to have a mismatched band offset. For example, when a second coating of ZnS was deposited on CdTe/CdSe (core/shell) nanocrystals, the emission was red-shifted, but the quantum efficiency decreased. Although ZnS layers can help passivate the CdSe shell layer surface, the effect was overwhelmed by the decreased wavefunction overlaps due to the electron wavefunction leakage into the ZnS layers.

The nanocrystal can be a member of a population of nanocrystals having a narrow size distribution. The nanocrystal can be a sphere, rod, disk, or other shape. The nanocrystal can include a core of a semiconductor material. The nanocrystal can include a core having the formula MX, where M is cadmium, zinc, magnesium, mercury, aluminum, gallium, indium, thallium, or mixtures thereof, and X is oxygen, sulfur, selenium, tellurium, nitrogen, phosphorus, arsenic, antimony, or mixtures thereof.

The semiconductor forming the core of the nanocrystal can include Group II-VI compounds, Group II-V compounds, Group III-VI compounds, Group III-V compounds, Group IV-VI compounds, Group I-III-VI compounds, Group II-IV-VI compounds, and Group II-IV-V compounds, for example, ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, or mixtures thereof.

The core can have an overcoating on a surface of the core. The overcoating can be a semiconductor material having a composition different from the composition of the core which is selected to provide a type II heterostructure. The overcoat of a semiconductor material on a surface of the nanocrystal can include a Group II-VI compounds, Group II-V compounds, Group III-VI compounds, Group III-V compounds, Group IV-VI compounds, Group I-III-VI compounds, Group II-IV-VI compounds, and Group II-IV-V compounds, for example, ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, or mixtures thereof. For example, ZnS, ZnSe or CdS overcoatings can be grown on CdSe or CdTe nanocrystals.

The emission from the nanocrystal can be a narrow Gaussian emission band that can be tuned through the complete wavelength range of the ultraviolet, visible, or infrared regions of the spectrum by varying the size of the nanocrystal, the composition of the nanocrystal, or both. For example, CdSe can be tuned in the visible region and InAs can be tuned in the infrared region.

The population of nanocrystals can have a narrow size distribution. The population can be monodisperse and can exhibit less than a 15% rms deviation in diameter of the nanocrystals, preferably less than 10%, more preferably less than 5%. Spectral emissions in a narrow range of between 10 and 150 nm full width at half max (FWHM) can be observed. Semiconductor nanocrystals having type II structures can have emission quantum efficiencies of greater than 2%, 5%, 10%, 20%, 40%, 60%, 70%, or 80%.

The absorption spectra of nanocrystals having type II heterostructures have characteristic features of smoothly increasing absorptions to the shorter wavelength region and long tails to the longer wavelength regions. This can be because the nanocrystals having type II structures have indirect band characteristics with spatially indirect excitons. Nanocrystals having type II structures can have relatively weak oscillator strength since the oscillator strengths are strongly governed by the carrier wavefunction overlaps. See, for example, Laheld, U. E. H., et al., *Phys. Rev. B* 1995, 52:2697, and Rorrison, J. M., *Phys. Rev. B* 1993, 48:4643, each of which is incorporated by reference in its entirety. Changes of the nanocrystal total oscillator strength before and after the shell growth can be compared because they are proportional to the spectrally integrated absorptivities of the nanocrystals. The nanocrystals having type II heterostructures can have near-infrared (near-IR) emissions, for example, in CdTe/CdSe (core/shell) and CdSe/ZnTe (core/shell) nanocrystals. These nanocrystals can be used as IR chromophores that are resistant against photo-bleaching and various chemical environments. In nanocrystals having type II heterostructures, both the cores and the shells have high probability densities for a carrier. As a result, thickness of the shell, as well as the core diameter, controls the emission energies due to the quantum confinement effect. By selecting different core diameters and shell thicknesses, the emission from type II nanocrystals can be easily tuned, for example, from 300 nm to 3 microns, or 700 nm to over 1000 nm. Nanocrystals having type II heterostructures can have longer exciton decay times than nanocrystals having type I heterostructures, for example, because spatially indirect excitons decay with much larger time constants.

Methods of preparing semiconductor nanocrystals include pyrolysis of organometallic reagents, such as dimethyl cadmium, injected into a hot coordinating agent. This permits discrete nucleation and results in the controlled growth of macroscopic quantities of nanocrystals. Preparation and manipulation of nanocrystals are described, for example, in U.S. Pat. No. 6,322,901, which is incorporated by reference in its entirety. The method of manufacturing a nanocrystal is a colloidal growth process and can produce a monodisperse particle population. Colloidal growth occurs by rapidly injecting an M donor and an X donor into a hot coordinating agent. The injection produces a nucleus that can be grown in a controlled manner to form a nanocrystal. The reaction mixture can be gently heated to grow and anneal the nanocrystal. Both the average size and the size distribution of the nanocrystals in a sample are dependent on the growth temperature. The growth temperature necessary to maintain steady growth increases with increasing average crystal size. The nanocrystal is a member of a population of nanocrystals. As a result of the discrete nucleation and controlled growth, the population of nanocrystals obtained has a narrow, monodisperse distribution of diameters. The monodisperse distribution of diameters can also be referred to as a size. The process of controlled growth and annealing of the nanocrystals in the coordinating agent that follows nucleation can also result in uniform surface derivatization and regular core structures. As the size distribution sharpens, the temperature can be raised to maintain steady growth. By adding more M donor or X donor, the growth period can be shortened.

An overcoating process is described, for example, in U.S. Pat. No. 6,322,901, which is incorporated by reference in its entirety. By adjusting the temperature of the reaction mixture during overcoating and monitoring the absorption spectrum of the core, overcoated materials having high emission quantum efficiencies and narrow size distributions can be obtained.

The M donor can be an inorganic compound, an organometallic compound, or elemental metal. The inorganic compound can be a salt. The salt can be combined with a coordinating agent, such as an amine. See, for example, U.S. Pat. No. 6,576,291, which is incorporated by reference in its entirety. M is cadmium, zinc, magnesium, mercury, aluminum, gallium, indium or thallium. The X donor is a compound capable of reacting with the M donor to form a material with the general formula MX. Typically, the X donor is a chalcogenide donor or a pnictide donor, such as a phosphine chalcogenide, a bis(silyl) chalcogenide, dioxygen, an ammonium salt, or a tris(silyl) pnictide. Suitable X donors include dioxygen, bis(trimethylsilyl) selenide (($TMS)_2Se$), trialkyl phosphine selenides such as (tri-n-octylphosphine) selenide (TOPSe) or (tri-n-butylphosphine) selenide (TBPSe), trialkyl phosphine tellurides such as (tri-n-octylphosphine) telluride (TOPTe) or hexapropylphosphorustriamide telluride (HPPTTe), bis(trimethylsilyl)telluride (($TMS)_2Te$), bis(trimethylsilyl)sulfide (($TMS)_2S$), a trialkyl phosphine sulfide such as (tri-n-octylphosphine) sulfide (TOPS), an ammonium salt such as an ammonium halide (e.g., $NH_4Cl$), tris(trimethylsilyl) phosphide (($TMS)_3P$), tris(trimethylsilyl) arsenide (($TMS)_3As$), or tris(trimethylsilyl) antimonide (($TMS)_3Sb$). In certain embodiments, the M donor and the X donor can be moieties within the same molecule.

A coordinating agent can help control the growth of the nanocrystal. The coordinating agent is a compound having a donor lone pair that, for example, has a lone electron pair available to coordinate to a surface of the growing nanocrystal. The coordinating agent can be a solvent. Solvent coordination can stabilize the growing nanocrystal. Typical coordinating agents include alkyl phosphines, alkyl phosphine oxides, alkyl phosphonic acids, or alkyl phosphinic acids, however, other coordinating agents, such as pyridines, furans, and amines may also be suitable for the nanocrystal production. Examples of suitable coordinating agents include pyridine, tri-n-octyl phosphine (TOP) and tri-n-octyl phosphine oxide (TOPO). Technical grade TOPO can be used.

Size distribution during the growth stage of the reaction can be estimated by monitoring the absorption line widths of the particles. Modification of the reaction temperature in response to changes in the absorption spectrum of the particles allows the maintenance of a sharp particle size distribution during growth. Reactants can be added to the nucleation solution during crystal growth to grow larger crystals. By stopping growth at a particular nanocrystal average diameter, a population having an average nanocrystal diameter of less than 150 Å can be obtained. A population of nanocrystals can have an average diameter of 15 Å to 125 Å.

The particle size distribution can be further refined by size selective precipitation with a poor solvent for the nanocrystals, such as methanol/butanol as described in U.S. Pat. No. 6,322,901, incorporated herein by reference in its entirety. For example, nanocrystals can be dispersed in a solution of 10% butanol in hexane. Methanol can be added dropwise to this stirring solution until opalescence persists. Separation of supernatant and flocculate by centrifugation produces a precipitate enriched with the largest crystallites in the sample. This procedure can be repeated until no further sharpening of the optical absorption spectrum is noted. Size-selective precipitation can be carried out in a variety of solvent/nonsolvent pairs, including pyridine/hexane and chloroform/methanol. The size-selected nanocrystal population can have no more than a 15% rms deviation from mean diameter, preferably 10% rms deviation or less, and more preferably 5% rms deviation or less.

The outer surface of the nanocrystal can include a layer of compounds derived from the coordinating agent used during the growth process. The surface can be modified by repeated exposure to an excess of a competing coordinating group to form an overlayer. For example, a dispersion of the capped nanocrystal can be treated with a coordinating organic compound, such as pyridine, to produce crystallites which disperse readily in pyridine, methanol, and aromatics but no longer disperse in aliphatic solvents. Such a surface exchange process can be carried out with any compound capable of coordinating to or bonding with the outer surface of the nanocrystal, including, for example, phosphines, thiols, amines and phosphates. The nanocrystal can be exposed to short chain polymers which exhibit an affinity for the surface and which terminate in a moiety having an affinity for a suspension or dispersion medium. Such affinity improves the stability of the suspension and discourages flocculation of the nanocrystal.

Transmission electron microscopy (TEM) can provide information about the size, shape, and distribution of the nanocrystal population. Powder X-ray diffraction (XRD) patterns can provided the most complete information regarding the type and quality of the crystal structure of the nanocrystals. Estimates of size are also possible since particle diameter is inversely related, via the X-ray coherence length, to the peak width. For example, the diameter of the nanocrystal can be measured directly by transmission electron microscopy or estimated from X-ray diffraction data using, for example, the Scherrer equation. It also can be estimated from the UV/Vis absorption spectrum.

EXAMPLES

All the procedures described here were carried out under an inert atmosphere unless specified otherwise. CdTe and CdSe nanocrystals were synthesized via pyrolysis of organometallic precursors using previously described procedures. See, for example, Murray, et al., *J. Am. Chem. Soc.* 1993, 115, 8706, and Mikulec, F. Ph.D. Thesis, MIT, 1999.

Preparation of Nanocrystals

Bis-(trimethylsilyl)selenide was prepared as follows. To 200 mL of a solution of superhydride (Aldrich, 1.0 M solution of lithium triethylborohydride in tetrahydrofuran), 7.89 g of Se shot (Strem, 99.99%) was added and stirred at room temperature for 2 hours. Chlorotrimethylsilane (25.2 g, Aldrich, 99%) was introduced and further stirred for a few hours. Solvents were removed in vacuo. The product was obtained by vacuum distillation.

A population of CdTe/CdSe (core/shell) nanocrystals was prepared as follows. Precipitated CdTe nanocrystals were dispersed in trioctylphosphine oxide (TOPO, Alfa, 95%), and dried under vacuum at 160° C. An overcoating stock solution was prepared by mixing desired amounts of 1:1 molar stoichiometry of dimethylcadmium (Strem, 97%) and bis(trimethylsilyl)selenide in trioctylphosphine (TOP, Fluka, 90%). While the CdTe-TOPO mixture was vigorously stirred under Ar flow, prepared overcoating stock solution was added slowly dropwise. Temperature was set at a point ranging from 130° C. to 180° C. depending on the size of CdTe nanocrystals used. A higher temperature was necessary for larger size CdTe nanocrystals.

Another population of CdTe/CdSe (core/shell) nanocrystals was prepared as follows. Precipitated CdTe nanocrystals were dispersed in a mixture of TOP and TOPO. The mixture was vigorously stirred and heated to 100° C., and overcoating stock solution prepared as above was then added slowly dropwise. The reaction mixture was stirred for 3 hours at 100° C. The formation of small CdSe nanocrystals (informally called "magic size" nanocrystals, with a peak absorbance at ~410 nm) was monitored by optical spectroscopy. The reaction temperature was raised to 200° C. and stirred until the CdSe shell growth is completed. The small "magic size" CdSe nanocrystals fused onto the CdTe nanocrystal core surface, forming a CdSe shell. The CdSe shell formation step took up to a few days.

A population of CdSe/ZnTe (core/shell) nanocrystals generally was prepared by the method described for CdTe/CdSe nanocrystals. Diethylzinc (Strem, 99.99%) and TOPTe were used as the precursors. TOPTe was made by dissolving Te powder (Strem, 99.999%) in TOP at room temperature.

Characterization of Nanocrystals

Figure 3:
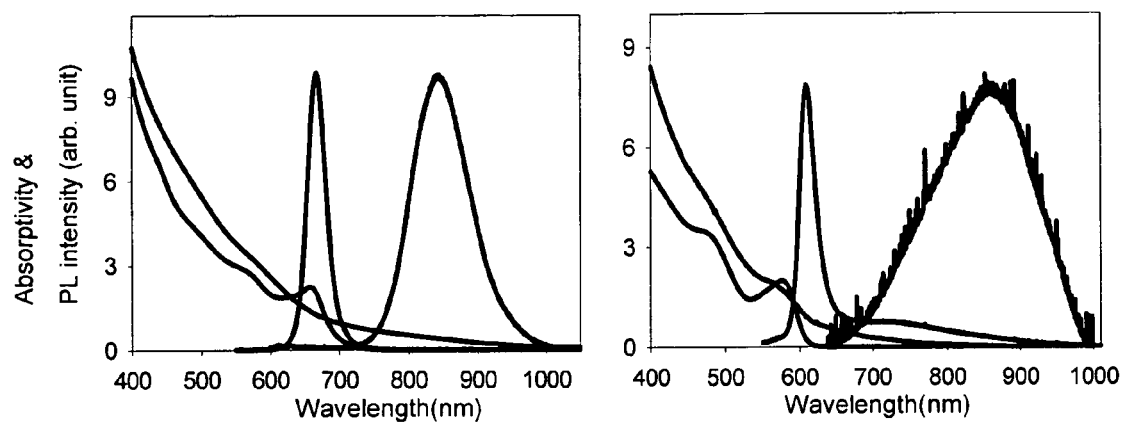
FIG. 3 are graphs depicting absorptivity and normalized photoluminescence spectra of nanocrystals.

FIG. 3 shows the absorption and emission spectra of core CdTe and CdSe nanocrystals and corresponding CdTe/CdSe (core/shell) and CdSe/ZnTe (core/shell) nanocrystals having a type II structure. The left graph shows spectra of 32 Å radius CdTe nanocrystals (dashed) and CdTe/CdSe (32 Å radius core/11 Å shell thickness) nanocrystals. The right graph shows spectra of 22 Å radius CdSe nanocrystals (dashed) and CdSe/ZnTe (22 Å radius core/18 Å shell thickness) nanocrystals. The photoluminescence spectra were obtained by exciting the nanocrystals at 533 nm. Changes of the nanocrystal total oscillator strength before and after the shell growth can be compared because they are proportional to the spectrally integrated absorptivities of the nanocrystals. The type II emission is not related to the deep trap luminescence of the core nanocrystals. In FIG. 3, deep trap luminescence of bare CdSe nanocrystals can be found around 750 nm, which does not match the emission wavelength of the corresponding CdSe/ZnTe (core/shell) nanocrystals having type II structures. This excludes the possibility that the deposition of shell layers merely quenches the band-edge luminescence of the cores while the deep trap luminescence remains.

Figure 4A:
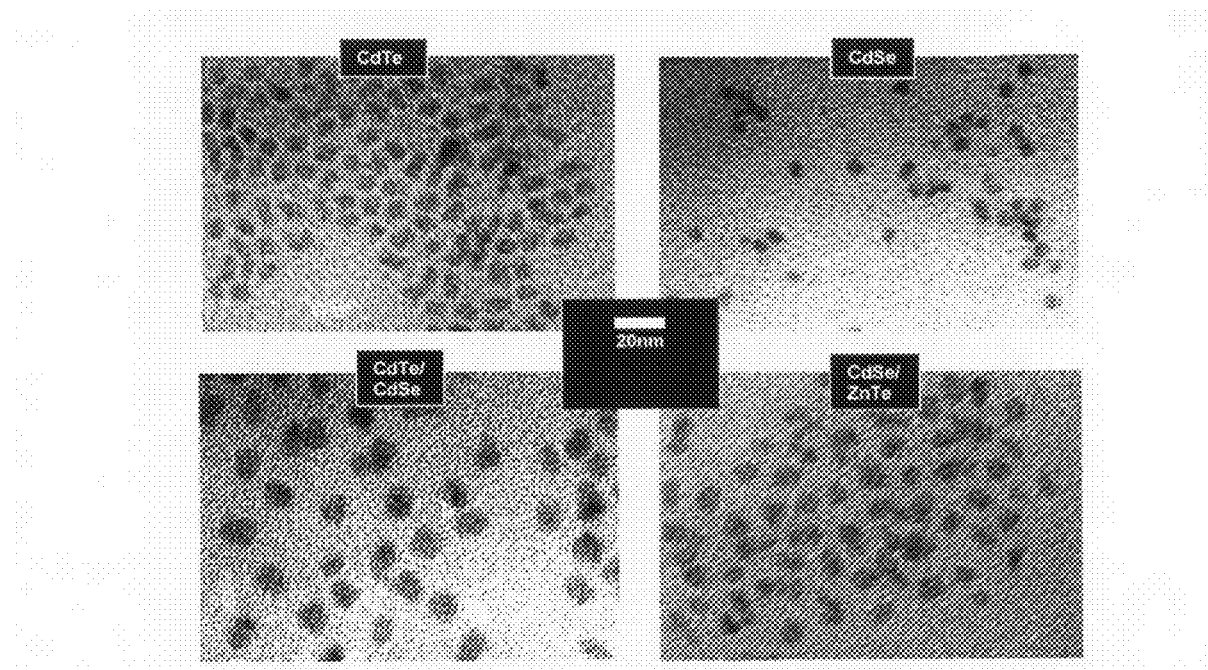
FIG. 4A are bright field transmission electron microscopy (TEM) images of nanocrystals.
Figure 4B:
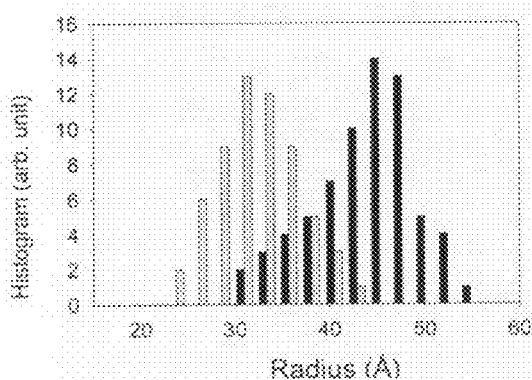
FIGS. 4B and 4C are graphs depicting size distributions of the nanocrystals.
Figure 4C:
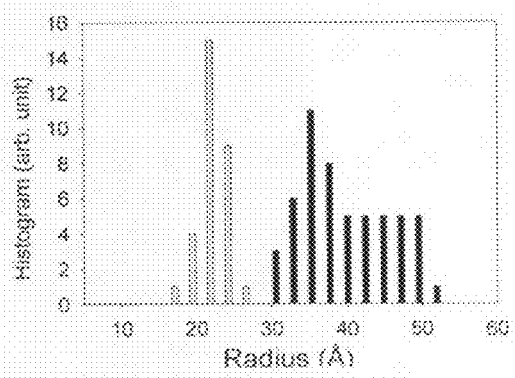

Actual particle size changes can be seen in the transmission electron microscopy (TEM) images of FIG. 4A. FIG. 4A generally shows samples that were used to obtain the spectra of FIG. 3, namely a monodisperse population of 32 Å radius CdTe nanocrystals, a monodisperse population of CdTe/CdSe (32 Å radius core/11 Å shell thickness) nanocrystals, a monodisperse population of 22 Å radius CdSe nanocrystals, and a monodisperse population of CdSe/ZnTe (22 Å radius core/18 Å shell thickness) nanocrystals. The images were obtained using a JEOL 2000 at an operation voltage of 200 kV. FIGS. 4B and 4C are graphs depicting size distributions of the nanocrystals. The total oscillator strengths of the nanocrystals did not change much as a result of shell growth despite of the significant increase in actual particle size. Increased number of crystalline unit cells in nanocrystals having type II structures compared to the corresponding core nanocrystals can be expected to result in much higher total oscillator strengths, but the effect is offset by the poor overlap between the electron and hole wavefunctions which is induced by the type II electronic structures. This effect is a characteristic feature of nanocrystals having type II structures that generally is not found in alloyed systems.

Figure 5A:
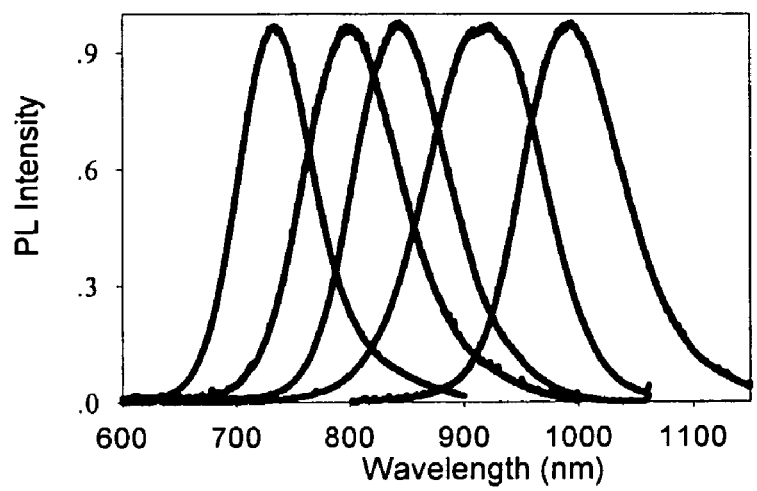
FIG. 5A is a graph depicting normalized photoluminescence spectra of a monodisperse population of different dimension CdTe/CdSe (core/shell) nanocrystals.
Figure 5B:
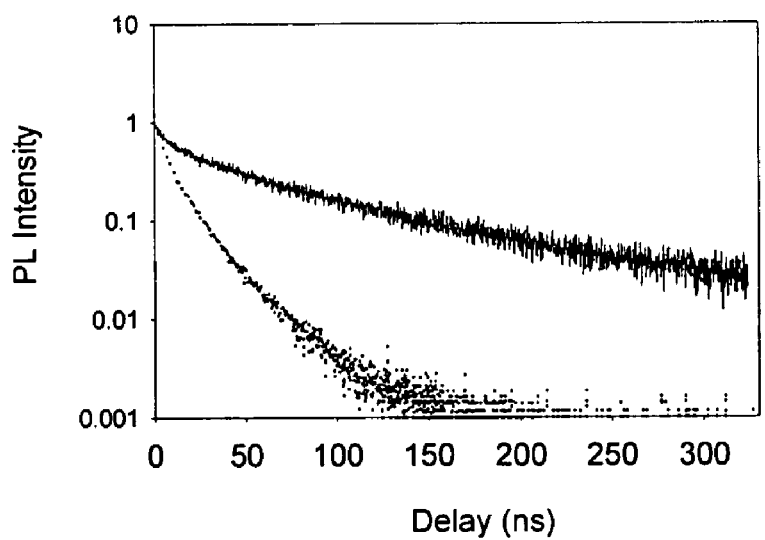
FIG. 5B is a graph of normalized photoluminescence intensity decays of a monodisperse population of CdTe/CdSe (core/shell) nanocrystals and a monodisperse population of CdTe nanocrystals.

With the two variables of the shell thickness and the core size, emissions of type II nanocrystals can be easily tuned. As seen in FIG. 5A, the emission of CdTe/CdSe (core/shell) nanocrystals can span from 700 nm to over 1000 nm simply by changing the core size and shell thickness. The CdTe core radii and CdSe shell thicknesses were 16 Å/19 Å, 16 Å/32 Å, 32 Å/11 Å, 32 Å/24 Å, and 56 Å/19 Å from left to right in the graph. The size of the core and shell thickness was measured via TEM and elemental analysis by wavelength dispersion spectroscopy (WDS). FIG. 5B shows room temperature PL decays of CdTe/CdSe (32 Å radius core/11 Å shell thickness) nanocrystals (solid line) and 32 Å radius CdTe nanocrystals (dotted line). The data were obtained by exciting the samples with a 400 nm pulse laser at 298 K. The PL decay of CdTe/CdSe (core/shell) nanocrystal was much longer than that of the core CdTe nanocrystal. This shows the characteristic long decay of spatially indirect excitons from nanocrystals having type II heterostructures.

Other embodiments are within the scope of the following claims.

What is claimed is:

1. A device comprising a coated nanocrystal comprising:
   a core nanocrystal including a first semiconductor material;
   an overcoating including a second semiconductor material on the core nanocrystal; and
   an organic layer on a surface of the coated nanocrystal,
   wherein the first semiconductor material and the second semiconductor material are selected so that, upon excitation, one charge carrier is substantially confined to the core and the other charge carrier is substantially confined to the overcoating.

2. The device of claim 1, wherein the conduction band of the first semiconductor material is at higher energy than the conduction band of the second semiconductor material and the valence band of the first semiconductor material is at higher energy than the valence band of the second semiconductor material.

3. The device of claim 1, wherein the conduction band of the first semiconductor material is at lower energy than the conduction band of the second semiconductor material and the valence band of the first semiconductor material is at lower energy than the valence band of the second semiconductor material.

4. The device of claim 1, wherein the organic layer is obtained by exposing the nanocrystal to an organic compound having affinity for a surface of the coated nanocrystal.

5. The device of claim 1, wherein the coated nanocrystal is dispersible.

6. The device of claim 1, where in the first semiconductor material is a Group II-VI compound, a Group II-V compound, a Group III-VI compound, a Group III-V compound, a Group IV-VI compound, a Group I-III-VI compound, a Group II-IV-VI compound, or a Group II-IV-V compound.

7. The device of claim 1, wherein the first semiconductor material ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, or mixtures thereof.

8. The device of claim 1, wherein the second semiconductor material is a Group II-VI compound, a Group II-V compound, a Group III-VI compound, a Group III-V compound, a Group IV-VI compound, a Group I-III-VI compound, a Group II-IV-VI compound, or a Group II-IV-V compound.

9. The device of claim 1, wherein the second semiconductor material is ZnO, ZnS, ZnSe, ZnTe, CdO, CdS, CdSe, CdTe, MgO, MgS, MgSe, MgTe, HgO, HgS, HgSe, HgTe, AlN, AlP, AlAs, AlSb, GaN, GaP, GaAs, GaSb, InN, InP, InAs, InSb, TlN, TlP, TlAs, TlSb, TlSb, PbS, PbSe, PbTe, or mixtures thereof.

10. The device of claim 1, wherein the nanocrystal emits light upon excitation, wherein the wavelength of maximum emission intensity is longer than 700 nm.

11. The device of claim 1, wherein the nanocrystal emits light upon excitation, wherein the wavelength of maximum emission intensity is between 700 nm and 1500 nm.

12. The device of claim 1, wherein the coated nanocrystal is a member of a population of coated nanocrystals comprising:
   a plurality of coated nanocrystals, each coated nanocrystal including a core nanocrystal and an overcoating on each core nanocrystal, wherein each core includes a first semiconductor material and each overcoating includes a second semiconductor material, the plurality of core nanocrystals forming a population of nanocrystals,
   wherein the first semiconductor material and the second semiconductor material are selected so that, upon excitation, one charge carrier is substantially confined to the core and the other charge carrier is substantially confined to the overcoating; and the plurality of nanocrystals is monodisperse.

13. The device of claim 1, wherein the device is a photovoltaic device or a photoconduction device.

14. A device comprising a coated nanocrystal comprising:
   a core nanocrystal including a first semiconductor material;
   a first overcoating including a second semiconductor material on the core nanocrystal; and
   a second overcoating including a third semiconductor material on the first overcoating,
   wherein the first semiconductor material and the second semiconductor material are selected so that, upon excitation, one charge carrier is substantially confined to the core and the other charge carrier is substantially confined to the first overcoating.

15. The device of claim 14, wherein the conduction band of the first semiconductor material is at higher energy than the conduction band of the second semiconductor material and the valence band of the first semiconductor material is at higher energy than the valence band of the second semiconductor material.

16. The device of claim 14, wherein the conduction band of the first semiconductor material is at lower energy than the conduction band of the second semiconductor material and the valence band of the first semiconductor material is at lower energy than the valence band of the second semiconductor material.

17. The device of claim 14, further comprising an organic layer on a surface of the coated nanocrystal.

18. The device of claim 14, wherein the device is a photovoltaic device or a photoconduction device.

19. A device comprising a coated nanocrystal comprising:
   a core nanocrystal including a first semiconductor material;
   a first overcoating including a second semiconductor material on the core nanocrystal; and
   a second overcoating including a third semiconductor material on the first overcoating,
   wherein the third semiconductor material has a mismatched band offset to the second semiconductor material.

* * * * *

UNITED STATES PATENT AND TRADEMARK OFFICE
CERTIFICATE OF CORRECTION

PATENT NO. : 7,825,405 B2  Page 1 of 1
APPLICATION NO. : 12/213001
DATED : November 2, 2010
INVENTOR(S) : Kim et al.

It is certified that error appears in the above-identified patent and that said Letters Patent is hereby corrected as shown below:

Col. 1 Line 15
In the section FEDERALLY SPONSORED RESEARCH OR DEVELOPMENT, delete the text "The U.S. Government may have certain rights in this invention pursuant to Contract No. N00014-01-1-0787 awarded by the Office of Naval Research." and insert -- This invention was made with Government support under Grant No. N00014-01-1-0787, awarded by the US Navy. The Government has certain rights in this invention. --

Signed and Sealed this
Tenth Day of May, 2011

David J. Kappos
*Director of the United States Patent and Trademark Office*